United States Patent [19]

Szantay et al.

[11] 4,199,505
[45] Apr. 22, 1980

[54] PROCESS FOR THE PREPARATION OF ALKALOIDS OF THE LEUROSINE TYPE

[75] Inventors: Csaba Szántay; Lajos Szabó; Katalin Honty; Katalin Nógrádi; Karola Jovanovics; Eszter Dezserti; Lajos Dancsi; Csaba Lórinez; Béla Szarvady; Lahos Kovács, all of Budapest, Hungary

[73] Assignee: Richter Gedeon Vegyeszeti Gyar Rt., Budapest, Hungary

[21] Appl. No.: 907,626

[22] Filed: May 19, 1978

[30] Foreign Application Priority Data

May 20, 1977 [HU] Hungary .................. RI 632

[51] Int. Cl.$^2$ .......................................... C07D 519/04
[52] U.S. Cl. ................................................ 260/244.4
[58] Field of Search ................... 260/287 B; 260/244.4

[56] References Cited

U.S. PATENT DOCUMENTS 3,716,541  2/1973  Dobson et al. .................. 260/287 B

FOREIGN PATENT DOCUMENTS 2558124  1/1976  Fed. Rep. of Germany .

OTHER PUBLICATIONS

March, "Advanced Organic Chemistry" (1968), pp. 618-621 and 720-721.

Morrison et al., "Organic Chemistry" (1966), pp. 885-887.

*Primary Examiner*—Donald G. Daus
*Assistant Examiner*—David E. Wheeler
*Attorney, Agent, or Firm*—Karl F. Ross

[57] ABSTRACT

A process for the preparation of alkaloids of the leurosine type having the formula I

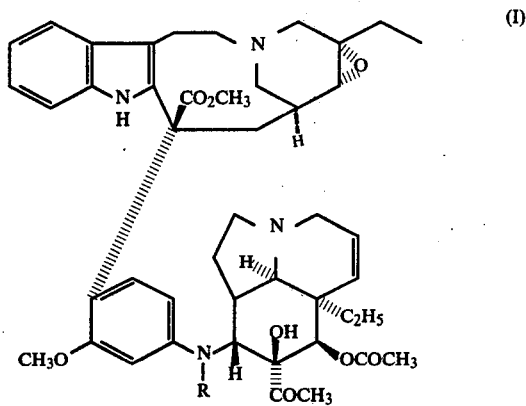

and the acid addition salts thereof. In the formula I R is hydrogen or methyl. The compounds prepared according to the invention are known compounds showing cytostatic activity.

12 Claims, No Drawings

PROCESS FOR THE PREPARATION OF ALKALOIDS OF THE LEUROSINE TYPE

The invention relates to a new process for the preparation of alkaloids of the leurosine type having the formula I

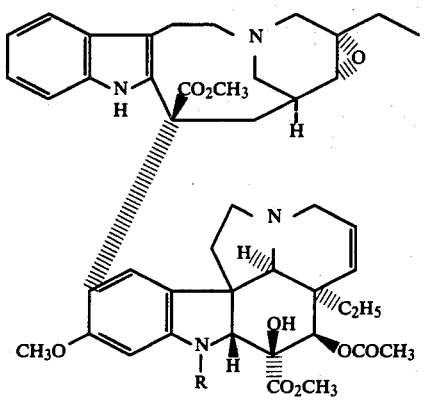

(I)

and the acid addition salts thereof. In the formula I R is hydrogen, methyl or formyl.

Alkaloids of the leurosine type having the formula I are known compounds with cytostatic activity. Until recently leurosine (a compound of the formula I, in which R=CH$_3$) was isolated from Vinca rosea L. by extraction [D. J. Abraham, N. R. Farnsworth: J. of Pharm. Sci. 58/6 694 (1969)].

The first semi-synthetic derivatives of leurosine, such as N-desmethyl-leurosine (R=-H) and N-desmethyl-N-formyl-leurosine (R=formyl) are disclosed in the Hungarian Patent specification No. 165,986 and in the corresponding British Patent Specification No. 1,412,932.

The first a total synthesis of diindole-type alkaloids has been made in the past two years. These methods are based on the coupling of the two fragments, i.e. of the vindoline and velbanamine moiety (e.g. catharantine) of the diindole alkaloid. According to POTIER et al's method [Tetrahedron Letters, 3945 (1976)] the various diindole alkaloids encompassed by the general formula I, in which R represents a methyl group, namely leurosine and derivatives thereof substituted at the C-14,15 positions of the vindoline moiety are produced by a method described hereinafter.

(A) Catharantine or an other velbanamine derivative is oxidized into a corresponding N-oxide with p-nitroperbenzoic acid, (B) the N-oxide obtained is coupled with a corresponding vindoline derivative of POLONOVSZKY reaction, to give an immonium salt having the diindole structure, which is then reduced into a corresponding 3',4'-anhydro-diindole-alkaloid derivative, (C) the obtained 3',4'-anhydro-diindole-alkaloid derivative is transformed into the N-oxide of a corresponding 3',4'-epoxy derivative, with p-perbenzoic acid, and finally (D) from the N-oxide group oxygen is eliminated with zinc in the presence of acetic acid.

The method has the following disadvantages. The anhydro derivative prepared in the first two (A)+(B) synthesis steps—drawing conclusions from the very low values of the specific rotation thereof—is extremely contaminated. A further drawback of the method is that in the synthesis step (C) the N-oxide of the desired epoxy derivative is obtained which should be decomposed in an additional step (step (D)).

The first two steps of the above synthesis are disclosed in the published German patent specification No. 25,58,124. This specification describes a very broadly defined general formula having substituents at all possible sites of the diindole molecule which covers all the possible N-methyl-, N-desmethyl- and N-formyl derivatives while in the disclosure only the synthesis of the N-methyl derivatives is sufficiently disclosed. And what is more, the method described is inoperative for the preparation of N-formyl derivatives. It is inoperative since (1) the appropriate vindoline derivative (N-desmethyl-N-formyl-vindoline) neither has been available from the prior art, nor was disclosed in the specification, (2) by bringing the formyl substituent of strongly electrophilic character into the vindoline moiety, the site of coupling becomes poor in electrons and consequently, the N-desmethyl-N-formyl-vindoline cannot be coupled with the appropriate catharantine derivative.

KUTNEY et al [Helv. Chim. Acta 59, 2858 (1976) and Heterocycles 4, 997 (1976)] use a very similar synthesis. The distinctive features of their synthesis over POTIER's method are as follows:

In the step (A) m-chloro-perbenzoic acid is used as an oxidizing agent, and, reaction (C) is performed with tert-butyl-hydroperoxide, in the presence of tetrahydrofuran. In the synthesis step (C) the nitrogen atom is protected in form of a trifluoro-acetic acid salt to avoid the formation of N-oxide, which makes the step (D) unnecessary.

This method has, however, also several disadvantages. The low melting point of anhydro derivative obtained after the steps A+B indicates a considerable contamination of the product. On the other hand, the temporary protection of the nitrogen atom in the step (C) requires the introduction of an additional reaction step, and the epoxidation does not always results in the desired product, as, the reaction is difficult to control.

The first two steps of the latter synthesis are protected in the Belgian Patent Specification No. 842,200, wherein the scope of protection is identical with the scope of compounds disclosed in the above article.

The object of this invention is to provide an operative synthesis method for the preparation of the leurosine-type compounds having the formula I, which is easy to accomplish on a large scale. A further aim is to decrease the number of the reaction steps and to eliminate any step difficult to control, as well as to improve the quality, especially the purity of the end products.

We have surprisingly found that substituting for aromatic per-acids in the reaction step (A) aliphatic per-acids having 6 to 18 carbon atoms, the purity of the N-oxide obtained and indirectly that of the end product is sufficiently increased. There is an especially favorable improvement in the quality of the 3',4'-anhydro-diindole compound. In some cases the specific rotation thereof increases by about 50° and the melting point by about 30° to 37° C.

By oxidizing vindoline we have prepared the N-desmethyl-N-formyl-vindoline which has subsequently been hydrolyzed into N-desmethyl-N-vindoline. N-desmethyl-vindoline, in contrast to the N-formyl derivative, can be coupled with the catharantine-N-oxide under the conditions of the POLONSZKY reaction (B)

reaction step)-This is the first process known for the synthesis of the above vindoline derivatives. N-desmethyl-N-formyl-vindoline has not been described in the art before. For the preparation of N-desmethyl-vindoline, on the other hand, a microbiological process is set forth in Helo. Chim. Acta 57, 1891 (1974).

It has further been found that performing the epoxidation in the reaction step (C) either by oxygen or an alkali metal hypohalogenite, in the presence of an organic solvent, or by organic peroxides, in the presence of compounds containing nitrile and/or azo groups, the formation of the N-oxide can be avoided, consequently the single electron pair of the nitrogen need not be protected before the reaction, and the additional reaction step to eliminate the N-oxide group can also be omitted. The product obtained in this way excels by its good crystallizability and purity. Measured by chromatography, even the crude product shows an excellent purity, and—unexpectedly for one skilled in the art—no N-oxidized product can be traced, in spite of the fact that the single electron pair of the nitrogen has not been previously protected.

A further advantage of the epoxidation according to the invention is its selectivity. The compound subjected to epoxidation contains two olefine bonds, but the epoxy group is formed only at the desired site, that is the epoxidation is regioselective.

In addition to this, the epoxy-ring can theoretically be formed in two different configurations but practically according to the invention only one of them, namely the isomer corresponding to the natural compound, is obtained, which means that the epoxidation is also stereoselective.

The yields are also improved. While the methods known in the art gave the product with a maximum yield of 51%, using the present method a yield of 63% can be achieved, which is a considerable economic advantage with respect to the extremely high price of the product.

Alternetively, compounds of the formula I, in which R is a formyl group can also be prepared starting from vincristine by the VILSMEIER-HAAK reaction, and a subsequent epoxidation. The reaction proceeds with an outstanding yield, and makes possible to prepare the more effective and less toxic N-desmethyl-N-formyl-leurosine from vincristine, on the other hand, provides a suitable tool to meet market-demands.

The object of the invention is to provide a process for the preparation of the compounds having the formula I and the acid addition salts thereof, wherein R stands for a hydrogen atom or for a methyl or formyl group.

According to the invention compounds of the formula I, wherein

R is hydrogen, methyl or formyl and the acid addition salts thereof are prepared by (a) reacting a compound of the formula III

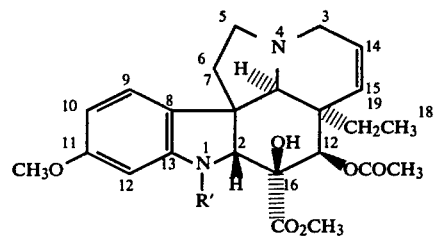

(III)

wherein R' is hydrogen or methyl, with catharantine-N-oxide and subsequently with an alkali metal borohydride in a manner known per se, and (a₁) epoxidizing a compound of the formula II

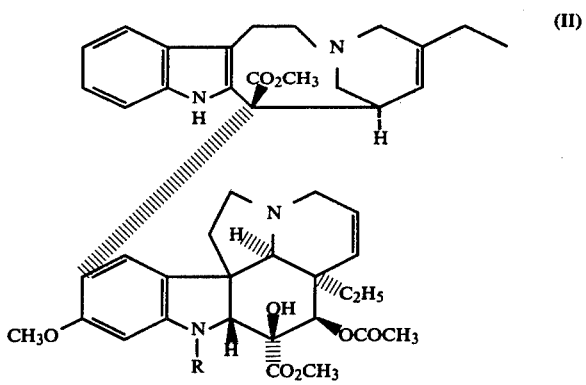

(II)

obtained, in which R is methyl, with oxygen or an alkali metal hypohalogenite in an organic solvent, or with an organic hydroperoxide in the presence of a compound containing nitrile and/or azo groups; or (a₂) epoxidizing a compound of the formula II obtained, in which R is hydrogen, with oxygen or an alkali metal hypohalogenite in an organic solvent, in the presence of an acid, or with an organic hydroperoxide in the presence of an acid and a compound containing nitrile and/or azo groups; or (a₃) reacting a compound of the formula II obtained, in which R is hydrogen, with a formylating agent, and epoxidizing a compound of the formula II prepared in this way, in which R is formyl, with oxygen or with an alkali metal hypohalogenite, or with an organic hydro peroxide in the presence of a compound containing nitrile and/or azo groups; or (b) treating vincristine or vinblastine or an acid addition salt thereof with a sulphur or phosphorous halide or oxyhalide in an organic solvent, and epoxidizing a compound of the formula II obtained, in which R is formyl or methyl with oxygen or with an alkali metal hypohalogenite in an organic solvent, or with an organic peroxide in an organic solvent, in the presence of a compound containing nitrile and/or azo groups; or (c) epoxidizing a compound of the formula II, wherein R stands for a hydrogen atom or a methyl or formyl group with oxygen or an alkali metal hypohalogenite in an organic solvent, and—when R is hydrogen—in the presence of an acid, or with an organic hydroperoxide in the presence of a compound containing nitrile and/or azo groups; and if desired, converting a compound of the formula I, in which R is hydrogen or methyl, obtained in any of the process varianets (a) to (c) to a corresponding compound of the formula I, wherein R represents a formyl group, in a manner known per se, and if desired, transforming a compound of the formula I obtained into an acid addition salt thereof.

According to process variant (a) catharantine-N-oxide and a compound of the formula III are used as starting compounds. Both of the starting compounds are known in the art. Catharantine and vindoline (a compound of the formula III, in which R' represents a methyl group) have at first been isolated from the plant Catharantus roseus G. Don [see J.Am. Pharm. Assoc. 48, 256 (1959)]. An other possible way for the preparation of the catharantine-N-oxide is disclosed in the Published German Patent Specification No. 25,58,124. The formula III as defined in the above publication encompasses also N-desmethyl-vindoline—R' is hydrogen—without describing the preparation of this compound.

According to process variant (a) by coupling vindoline or N-desmethyl-vindoline with catharantine-N-oxide first compounds of the formula (II) in which R stands for hydrogen or methyl group can be prepared. The product obtained is then epoxidized and optionally formylated in a second step, when any of the compounds of the formula I, wherein R is hydrogen, methyl or formyl, can be prepared.

A method of implementation of the process variant (a) according to the invention consists in preparing a compound of the formula II, wherein R is hydrogen. In this case vindoline is at first transformed into N-desmethylvindoline by oxidation carried out with a metal oxide, preferably with manganese dioxide. The oxidation is accomplished in an organic solvent, suitably in a chlorinated hydrocarbon, for instance in dichloromethane, dichloroethane or chloroform. It is preferred to perform the oxidation below 25° C., preferably in the range of about 5° C. to 10° C.

N-desmethyl-N-formyl-vindoline obtained by oxidation is transformed into N-desmethyl-vindoline by hydrolysis. Hydrolysis is suitably effected with an acid, preferably with a mineral acid, e.g. hydrochloric acid, sulphuric acid etc. According to a further advantageous method vindoline is directly desmethylated to give N-desmethyl-vindoline.

N-desmethyl-vindoline prepared by any of the methods outlined above is reacted with catharantine-N-oxide. Catharantine-N-oxide may be prepared by any of the known methods, but preferably is obtained by oxidizing catharantine with aliphatic per-acids having six to 18 carbon atoms, for instance with peroctanic acid, perpelargonic acid or perlaurinic acid. The oxidation is accomplished in an organic solvent, preferably in a chlorinated hydrocarbon, in the temperature range of about −30° to 25° C.

N-desmethyl-vindoline is reacted with catharantine-N-oxide prepared in situ in the presence of trifluoroacetic-anhydride, and the diindole-immonium salt obtained in reduced with an alkali metal borohydride. Although this reaction route is known as POLONOVSZKY reaction it has never been used before for coupling catharantine-N-oxide and N-desmethyl-vindoline.

According to a further preferred variant of the process(a), a compound of the formula II, in which R is methyl is prepared. In this case vindoline is reacted with catharantine-N-oxide in an analogous way to the one described above.

The compounds of the formula II, wherein R is a methyl group or a hydrogen atom, obtained in the above reactions, are transformed to the corresponding compounds having the formula I according to the process variant (a) by epoxidation. The compound of the formula II, wherein R is hydrogen is epoxidized in the presence of an acid, e.g. trifluoroacetic acid. The compound of the formula II, in which R is hydrogen, can be transformed, however, at first into the corresponding N-formyl compound according to process variant (a$_3$) which is then epoxidized. Apart form this the epoxidation is carried out in the reaction variants (a$_1$), (a$_2$) and (a$_3$) as well as (c) in the same way.

If oxygen, suitably oxygen from the air or an alkali metal hypohalogenide is used as an epoxidizing agent, the reaction can be carried out practically in any orgaic solvent stereo- and regioselectively. Examples of suitable solvents are tetrahydrofuran and organic amino compounds, for instance dimethyl formamide. If desired, complex metal compounds, e.g. vanadium-acetylacetonate or cobalt-naphthenate, or metal or metal oxide catalysts, e.g. black platinum or aluminum oxide can be used as promotors. The reaction can also be performed in a solvent of the nitrile type, and can optionally be promoted by the addition of radical initiators.

If the epoxidizing agents are organic peroxide such as coumyl- or t-butyl-hydroperoxide, the epoxidation is carried out in the presence of compounds containing nitrile- and/or azo-group(s). These compounds may act as solvents and/or radical initiators. Typical representatives of these compounds are the nitriles of aliphatic acids containing one to five carbon atoms, e.g. acetonitrile and isobutyronitrile, or the nitriles or aromatic acids, e.g. benzonitrile. 2,2'-azo-bis-isobutyronitrile, 2-cyano-2-propyl-azo-formamide, 2,2'-azo-bis-2-cyclohexyl-propionitrile and triazobenzene can also be used for the above purpose. Compounds of the formula (II) in which R is hydrogen, are epoxidized in the presence of an acid, preferably organic acid, such as trifluoroacetic acid.

The compounds of the formula I produced by the epoxidation, in which R is hydrogen or a methyl group, are isolated from the reaction mixture by conventional means, such as extraction or evaporation, and the final compounds are transformed, if desired, to their acid addition salts also by known methods.

The compounds of the formula I, in which R is hydrogen can be transformed into a corresponding compound, in which R is formyl, by formylation. Formylation is accomplished with formic acid or a reactive derivative thereof, or with a mixture of formic acid and acetic anhydride. The reaction temperature is below 30° C., preferably between −5° C. and 10° C.

The compound of the formula I, wherein R is methyl may be transformed, if desired, into a corresponding compound, in which R is formyl, in a manner known per se, preferably as described in Example 22, hereinafter.

According to the process variant (b) the compound of the general formula II in which R is a formyl group is produced by splitting off water from vincristine. Vincristine is treated with a sulphuric or phosphorous halogenide or phosphorous oxy-halogenide, in an organic solvent, preferably having a proton acceptor character. Suitably thionyl halogenide, phosphorous tri- or pentahalogenides or phosphorous oxi-halogenides are used for this purpose.

The removal of water is carried out in an organic solvent. Typical examples of suitable solvents are for example benzene homologs, such as benzene, toluene, xylene; aliphatic or cyclic ethers, such as diethyl ether or dioxane; and organic solvents having proton acceptor character, suitably organic bases containing nitrogen or acylated derivatives thereof, such as pyridine, piperidine or their acylated derivatives; aliphatic carboxylic acid amides having one to five carbon atoms; or an N-disubstituted derivative of any of these amids, such as dimethyl formamide, dimethyl acetamide, N-formyl-N-methyl-aniline etc. Suitable mixtures of the above inert and proton acceptor-type organic solvents can also be used.

According to a preferred embodiment of the process variant (b) the removal of water is carried out with thionyl chloride or phosphorous oxychloride, in the presence of dimethyl formamide. If desired, the polar complex, deriving from the interaction of the halogen compound and the solvent of proton acceptor character can be isolated, and used as reactant in the presence of any of the above described solvents. The reaction is preferably accomplished in a nitrogen atmosphere at a temperature of $-10°$ to $30°$ C.

The compound obtained is epoxidized according to the reaction ($a_1$) or ($a_3$).

The compounds of the formula I prepared by any of the process variants according to the invention, if desired, can be transformed into their acid addition salts.

The invention can be more fully understood by the following examples which are for illustration only.

EXAMPLE 1

N-desmethyl-N-formyl-vindoline 2.00 g. (4.38 mmoles) of vindoline are dissolved in 200 ml. of dry dichloromethane and 50.0 g. of activated manganese (IV)oxide (produced by Merck) are added to the solution. The reaction mixture is vigorously stirred in a nitrogen atmosphere, at $0°$ to $5°$ C. for ten hours and subsequently filtered. The oxidizing agent filtered off is washed with 100 ml. of dichloromethane and the filtrate evaporated to dryness under reduced pressure. The residue is purified by preparative thin layer chromatography (adsorber: silica gel $PF_{254+366}$; solvent: 100:10 mixture of dichloromethane and methanol; eluent: acetone). From the layer having a higher retention factor 0.50 g. (25%) of unreacted vindoline are recovered which can be used up repeatedly upon crystallization from ether. From the layer having a lower retention factor, after evaporating the acetone eluate and triturating the residue with ether, the title compound is obtained.

Yield: 0.70 g. (34.0%) of N-desmethyl-N-formyl-vindoline Melting point: $140°$ to $144°$ C. (crystallized from ether)

IR spectrum (KBr): 3500 cm$^{-1}$ /$\nu$ OH/, 1760 cm$^{-1}$ /$\nu$ $CO_2CH_3$, $OCOCH_3$/, 1695 cm$^{-1}$ /$\nu$ amide CO/, 1630 cm$^{-1}$ /$\nu$ C=C/.

$^1$H-NMR spectrum /$CDCl_3$/:

$\delta = 8.65$ /1H, s, N-C$\underline{H}$O/, 3.82 /3H, s, $CO_2CH_3$/; 3.70 /3H, s, $OCH_3$/; 2.01 ppm /3H, s, $OCOC\underline{H}_3$/.

$^{13}$C-NMR spectrum /$CDCl_3$/: 170.03 /$CO_2CH_3$ és OCO/; 161.07 /$C_{11}$/; 160.42 /N-CHO/; 142.00 /$C_{13}$/; 130.23 /$C_{15}$/; 125.21 /$C_8$/; 124.57 /$C_{14}$/; 124.16 /$C_9$/; 111.17 /$C_{10}$/; 97.19 /$C_{12}$/; 97.10 /$C_2$/; 76.75 /$C_{16}$/; 72.34 /$C_{17}$/; 71.50 /$C_{18}$/; 65.25 /$C_{21}$/; 55.65 /$OCH_3$/; 52.66 /$C_7$/; 52.60 /$CO_2CH_3$/; 50.43 /$C_3$/; 49.91 /$C_5$/; 42.43 /$C_{20}$/; 41.02 /$C_6$/; 30.31 /$C_{19}$/; 20.88 /$OCOCH_3$/.

Mass spectrum m/e /%/: 470 /M$^+$, 20/; 442 /5/; 441 /3/; 427 /3/; 411 /9/; 393 /2/; 383 /6/; 381 /6/; 369 /2/; 353 /1/; 351 /3/; 339 /1/; 323 /7/; 321 /4/; 311 /23/; 309 /15/; 203 /17/; 202 /26/; 188 /17/; 174 /65/; 160 /56/; 159 /22/; 158 /13/; 131 /20/; 130 /20/; 121 /100/.

EXAMPLE 2

N-desmethyl-vindoline 540 ml. (1.19 mmoles) of N-desmethyl-N-formyl-vindoline are dissolved in 110 ml. of a 10% solution of hydrochloric acid in methanol in nitrogen atmosphere, at $0°$ C. The reaction mixture is allowed to stand at $5°$ to $10°$ C. for three hours and then the pH of the solution is adjusted to 7 by adding a 10% solution of ammonia in methanol, with cooling. The neutralized solution is evaporated to 20 ml. under reduced pressure and 30 ml. of ice-water are added to the residue followed by the addition of a 1:1 mixture of water and ammonium hydroxide sufficient to set the pH-value to 9. The alkaline solution is extracted with three 20-ml. portions of dichloromethane, the dichloromethane extracts are combined, dried with magnesium sulphate and filtered. The filtrate is evaporated under reduced pressure. The residue is crystallized from 10 ml. of diethyl ether.

Yield: 400 mg. (78.7%) of N-desmethyl-vindoline Melting point: $118°$ C. (crystallized from ether).

IR spectrum (KBr): 3320 cm$^{-1}$ /$\nu$ NH,OH/, 1760 cm$^{-1}$ /$CO_2CH_3$; $OCOCH_3$/, 1630 cm$^{-1}$ /$\nu$ C=C/.

Mass spectrum m/e /%/: 442 /M$^+$, 17/; 383 /7.6/; 295 /2.9/; 282 /58/; 175 /62/; 174 /51/; 160 /15/; 147 /16/; 135 /87/; 122 /58/; 121 /100/.

$[\alpha]_D = -38.10°$ (C=0.76 chloroform).

$^1$H-NMR spectrum /$CDCl_3$/: $\delta = 6.98$, 6.85, 6.15 /3H, aromatic protons/; 5.98–5.18 /2H, olefin protons/; 5.55 /1H, s, 17-H/; 4.58 /1H, OH, disappears upon $D_2O$/; 4.15 /1H, NH/; 3.65 /6H, s, $CO_2CH_3$, $OCH_3$/2.09 /3H, s, $OCOC\underline{H}_3$/.

EXAMPLE 3

N-desmethyl-vindoline

Following the procedure of Example 2 but carrying out the hydrolysis in the presence of a 2% aqueous sulphuric acid solution instead of hydrochloric acid, and keeping the temperature at $5°$ C. the named compound is obtained.

Yield: 79.1%.

EXAMPLE 4

N-desmethyl-3',4'-anhydro-vinblastine 340 mg. (1.01 mmoles) of catharantine are dissolved in 17 ml. of dry dichloromethane. The solution is cooled to $-10°$ C. and 240 mg. of 82% perpelargonic acid (1.1 equivalents) in 3 ml. of dichloromethane are added under stirring, in a nitrogen atmosphere, within approximately 15 minutes. The reaction mixture is cooled to $-15°$ C. whereupon 442 mg. (1.0 mmoles) of N-desmethyl-vindoline and subsequently 0.82 ml. (5.8 mmoles) of trifluoro-acetic anhydride distilled freshly are added. The reaction mixture is allowed to stand at a temperature between $-10°$ and $-20°$ C. for 18 hours, and then 140 mg. of sodium borohydride dissolved in 14 ml. of dry methanol are added to the reaction mixture at $-10°$ C. The reaction is monitored by thin layer chromatography (adsorber: silica gel G; solvent: 20:2 mixture of dichloromethane and methanol). When the reaction is completed, the reaction mixture is concentrated to one fourth of its original volume at a bath temperature of $20°$ C. Thereafter 15 ml. of dichloromethane are added to the residue and the pH-value is adjusted to 9 with a 1:1 mixture of water and ammonium hydroxide. The phases are separated and the dichloromethane phase washed with two 10-ml. portions of water. The combined aqueous phases are extracted with two 10-ml. portions of dichloromethane. The dichloromethane phases are combined, dried with magnesium sulphate, filtered and the filtrate is evaporated to dryness under reduced pressure. The residue is pufified with preparative thin layer chromatography (adsorber, solvent and eluent as described in Example 1). The acetone solution of the product is evaporated and the product recrystallized from ethanol.

Yield: 315 mg. (40.2%) of N-desmethyl-3',4'-anhydro-vinblastine.

Melting point: 202° to 204° C. (dec.)

$[\alpha]_D^{20} = +38.5°$ (c=1.06, chloroform).

IR spectrum (KBr): 3400 cm$^{-1}$ /ν NH,OH/, 1740 cm$^{-1}$ /CO$_2$CH$_3$, OCOCH$_3$/, 1620 cm$^{-1}$ /νC=C/.

Mass spectrum m/e /%/: 778 /M+/.

EXAMPLE 4a

3',4'-anhydro-vinblastine

Following the procedure described in Example 4 but reacting catharantine N-oxide with vindoline in place of N-desmethyl vindoline, 50.0% of the named compound are obtained.

M.p.: 215° to 216° C.

$[\alpha]_D = +71°$ (c=0.7, chloroform).

Molar weight: 792.

EXAMPLE 5

N-desmethyl-3',4'-anhydro-vinblastine-sulphate 0.1 g. of N-desmethyl-3',4'-anhydro-vinblastine are suspended in 1 ml. of dry methanol and the pH-value of the suspension is adjusted to 5 by adding 1% methanolic sulphuric acid solution. The sulphuric addition salt is precipitated from the solution with 3 ml. of diethyl ether, and the precipitated crystals are filtered off and dried.

Yield: 95% named compound

Melting point: 210° C. (decomp.)

EXAMPLE 6

N-desmethyl-N-formyl-3',4'-anhydro-vinblastine 260 mg. (0.33 mmoles) of N-desmethyl-3',4'-anhydro-vinblastine are dissolved in 3 ml. of a 6:1 mixture of formic acid and acetic anhydride. The solution is allowed to stand at a temperature of five to 10° C. for 16 hours. The reaction mixture is poured onto 10 ml. of ice-water and its pH-value is adjusted to 9 with a concentrated aqueous ammonium hydroxide solution. The alkaline solution is extracted with three 6-ml. portions of benzene, the benzene extracts are combined, dried with magnesium sulphate and filtered. The filtrate is evaporated under reduced pressure and the residue crystallized from 1.5 ml. of methanol.

Yield: 190 mg. (70.5%) named compound.

Melting point: 208° C. (decomp.)

IR spectrum (KBr): 3400 cm$^{-1}$ /ν NH,OH/, 1730 cm$^{-1}$ /ν CO$_2$CH$_3$,OCOCH$_3$/, 1690 cm$^{-1}$ /ν N-CHO/, 1618 cm$^{-1}$ /ν C=C/.

$[\alpha]_D^{20} = +72.2°$ (c=1.01, chloroform).

Mass spectrum m/e /%/: 806 (M+).

EXAMPLE 7

N-desmethyl-N-formyl-leurosine

To a solution of 100 mg. (0.124 mmoles) of N-desmethyl-N-formyl-3',4'-anhydro-vinblastine in 3 ml. of benzonitrile 4 mg. of 2,2'-azo-bis-isobutyronitrile are added. The reaction mixture is cooled to a temperature between 0° and 5° C. and 160 mg. (0.75 mmoles) of 70% coumyl hydroperoxide dissolved in 1 ml. of benzonitrile are added under stirring, in a nitrogen atmosphere. The reaction mixture is allowed to stand at 5° to 10° C. for four days, in a nitrogen stream, whereupon 6 ml. of benzene are added and the reaction mixture is extracted with three 5-ml. portions of a 2.5% aqueous sulphuric acid solution at 0° to 5° C. The phases are separated. The acidic phase is shaken with 2 ml. of benzene and the phases are allowed to separate. The pH of the acidic solution is adjusted to 9 with a concentrated aqueous ammonium hydroxide solution at 0° C. The alkaline solution obtained is extracted with three 4-ml. portions of dichloromethane. The organic extracts are combined, dried with magnesium sulphate and evaporated under reduced pressure. The residue is crystallized from 1 ml. of methanol.

Yield: 55 mg. (54%) of the title compound.

Melting point: 203° C. (decomp.)

IR spectrum (KBr): 3400 cm$^{-1}$ /ν NH,OH/, 1730 cm$^{-1}$ /ν CO$_2$CH$_3$, OCOCH$_3$/, 1700 cm$^{-1}$ /νN-CHO/.

$[\alpha]_D^{20} = +79.5°$ /c=0.60, chloroform/.

Mass spectrum m/e /%/: 822 /M+/.

EXAMPLE 8

N-desmethyl-N-formyl-leurosine sulphate 0.1 g. of N-desmethyl-N-formyl-leurosine are dissolved in 0.5 ml. of dry ethanol and the pH of the solution is adjusted to 4 with a 1% solution of sulphuric acid in ethanol. The mixture is allowed to stand at room temperature for several hours, the sulphuric acid addition salt separated is filtered off and dried.

Yield: 93% title compound.

Melting point: 248° to 252° C.

EXAMPLE 9

N-desmethyl-leurosine

To a solution of 100 mg. (0.128 mmoles) of N-desmethyl-3',4'-anhydro-vinblastine in 3 ml. of dry acetonitrile there are added 29.0 mg. (0.25 mmoles) of trifluoro-acetic acid and 4 mg. of 2,2'-azo-bis-isobutyronitrile. The reaction mixture is cooled to 0° to 5° C. and 160 mg. (0.75 mmoles) of 70% coumyl-hydroperoxide in 1 ml. of dry acetonitrile are added with stirring, in nitrogen atmosphere. It is then allowed to stand for 22 hours in the nitrogen atmosphere and subsequently diluted with 6 ml. of dry benzene. The product is separated from the reaction mixture as described in the Example 7, crystallized from 1 ml. of methanol, and the crystals are filtered off and dried. 40 mg. of the title compound are obtained. A further 10-mg. portion of the named compound is obtained from the methanolic mother liquor by preparative thin layer chromatography (adsorber and solvent as described in the Example 1).

Total yield: 50 mg. (48%) of N-desmethyl-leurosine

Melting point: 221° C. (crystallized from methanol)

IR spectrum (KBr): 3460 cm$^{-1}$, 3380 cm$^{-1}$ /ν NH,OH/, 1735 cm$^{-1}$, 1738 cm$^{-1}$ /ν CO$_2$CH$_3$, ν OCOCH$_3$/.

$[\alpha]_D^{20} = +49.7°$ /c=0.98, chloroform/.

Mass spectrum m/e: 794 /M+/.

EXAMPLE 10

N-desmethyl-N-formyl-leurosine

A solution of 1 g. of N-desmethyl-leurosine in a mixture of 6 ml. of concentrated formic acid and 1 ml. of acetic anhydride is allowed to stand at room temperature for 10 minutes. The mixture is then poured into 30 ml. of water having a temperature of 0° to +5° C. and it is alkalized to pH 9 with cold, concentrated aqueous ammonium hydroxide solution. The alkaloid is extracted from the aqueous solution with three 30 ml.-portions of methylene chloride and the combined and dried methylene chloride solution is evaporated to dryness under reduced pressure.

Yield: 995 g. of N-desmethyl-N-formyl-leurosine

EXAMPLE 11

N-desmethyl-N-formyl-3',4'-anhydro-vinblastine

To a solution of 600 mg. (0.65 mmoles) of vincristine sulphate in 9 ml. of dry dimethyl formamide 1.2 ml. of thionyl chloride dissolved in 3 ml. of dimethyl formamide are added with external ice cooling. The reaction mixture is allowed to stand at room temperature for two hours, poured into ice-water and adjusted to pH 9 with a concentrated aqueous ammonium hydroxide solution. The alkaline solution is extracted with three 10-ml. portions of benzene, the combined benzene extracts are dried with magnesium sulphate, filtered and the filtrate is evaporated under reduced pressure. The residue is crystallized from 2 ml. of methanol.

Yield: 300 mg. (57%) of the named compound

The physical characteristics of this compounds are identical with those of the product of the Example 6. The title compound may be transformed into N-desmethyl-N-formyl-leurosine following the procedure described in the Example 7.

EXAMPLE 11a

3',4'-anhydro-vinblastine

Following the procedure described in Example 11 but starting from vinblastine sulphate instead of vincristine sulphate, the named compound is obtained.

Yield: 55%.
M.p.: 205° to 210° C.
$[\alpha]_D = +65.3°$ C. (c=0.66 chloroform)
Molar weight: 792.

EXAMPLE 12

200 mg. (0.25 mmoles) of (+)-3',4'-anhydro-vinblastine are dissolved in a mixture of 6 ml. of dry acetonitrile and 0.3 ml. of dry benzene. The reaction mixture is cooled to 0° to 5° C. and there are added 320 mg. of 70% coumyl hydroperoxide (1.5 mmoles) dissolved in 1 ml. of acetonitrile with stirring, in a nitrogen atmosphere. The reaction is monitored by thin layer chromatography and the reaction mixture is stirred till the reaction terminates (about 3 to 8 hours) at room temperature. Thereafter 14 ml. of dry benzene are added to the reaction mixture and the mixture obtained is extracted with three 10-ml. portions of a 2.5% aqueous sulphuric acid solution. The acidic phases are combined, extracted with 5 ml. of benzene and the pH-value of the acid phase is adjusted to 9 with a concentrated aqueous ammonium hydroxide solution. The alkaline solution prepared is extracted with three 8-ml. portions of dichloromethane, the organic phases are combined, dried with magnesium sulphate, filtered and the filtrate is evaporated under reduced pressure. 1 ml. of methanol is added to the residue, and the methanolic solution is allowed to crystallize. The crystals are filtered off and dried.

Yield: 102 mg. (50%) of (+)-leurosine
Melting point: 202° to 204° C.
$[\alpha]_D^{20} = +76°$ (c=0.9; chloroform); Mass spectrum m/e: 808 /M+

EXAMPLE 13

(+)-leurosine

Following the procedure described in the Example 12 but adding also 4.0 mg. of 2,2'-azo-bis-isobutyronitrile to the reaction mixture during the oxidation effected with peroxide, 128 mg. (62.7%) of the named compound are obtained.

EXAMPLE 14

(+)-leurosine

To a solution of 100 mg. (0.12 mmoles) of (+)-3',4'-anhydro-vinblastine in a mixture of 3 ml. of dry acetonitrile and 0.15 ml. of dry benzene there are added 4 mg. (0.02 mmoles) of 2,2'-azo-bis-isobutyonitrile. The reaction mixture is cooled to 0° to 5° C. and 80 mg. of 80% tert-butyl-hydroperoxide (0.7 mmoles) in a 0.5 ml. of acetonitrile are added with stirring, in nitrogen atmosphere. It is allowed to stand at room temperature for 8 hours and subsequently at −15° C. for 14 hours, with stirring. The precipitatous solution is filtered, washed with 0.5 ml. of acetonitrile (0° C.) and dried. 43 mg. of leurosine are obtained (1st fraction). The mother liquor is concentrated to 0.5 ml. at a water bath of 20° C., under reduced pressure. The residue is cooled to −15° C., allowed to stand for 24 hours, the precipitated crystals are filtered off, washed with acetonitrile or methanol and dried. 21 mg. of leurosine are obtained (2nd fraction) Total yield: 64 mg. (63%) of the named compound.

EXAMPLE 15

(+)-leurosine

To a solution of 200 mg. (0.25 mmoles) of (+)-3',4'-anhydro-vinblastine in 4 ml. of benzonitrile 8 mg. (0.048 mmoles) of 2,2'-azo-bis-isobutyronitrile are added. The reaction mixture is cooled to 0° to 5° C. and 320 mg. of coumyl-hydroperoxide (1.5 mmoles) in 1 ml. of benzonitrile are added with stirring, in a nitrogen atmosphere. By then following the procedure of the Example 12 104 mg. (51%) of the named compound are obtained.

EXAMPLE 16

N-desmethyl-N-formyl-leurosine 100 mg. (0.124 mmoles) of N-desmethyl-N-formyl-3',4'-anhydro-vinblastine are dissolved in 3 ml. of benzonitrile, 4 mg. of 2,2'-azo-bis-isobutyronitrile are added to the solution and it is stirred for three days at room temperature, in an oxygen atmosphere. 6 ml. of dry benzene are then added to the reaction mixture which is extracted with three 5-ml. portions of a 2.5% aqueous sulphuric acid solution cooled to 0.5° C. The organic phase is extracted with 2 ml. of benzene, and the phases are separated. The pH of the acid phase is adjusted to 9 with a concentrated aqueous ammonium-hydroxide solution under ice cooling, and the alkaline solution obtained is extracted with three 4-ml. portions of dichloromethane. The combined dichloromethane phases are dried with magnesium sulphate, filtered and the filtrate is evaporated under reduced pressure. The residue is crystallized from 1 ml. of methanol.

Yield: 50 mg. (49%) of the named compound.

EXAMPLE 17

N-desmethyl-N-formyl-leurosine

Following the procedure described in the Example 16 but carrying out the oxidation in the presence of 10 mg. of vanadium-acetyl-acetonate the reaction terminates within three hours to give 31 mg. (30% of the named compound.

EXAMPLE 18

Leurosine 100 mg. of 3',4'-anhydro-vinblastine are oxidized with oxygen from the air in an analogeous manner to that set forth in the Example 16, with the only difference that the reaction is performed in the presence of 4 mg. of 2,2'-azo-bis-isobutyronitrile.

Yield: 45 mg. (44%) of the named compound.

EXAMPLE 19

Leurosine 0.6 g. of 3',4'-anhydro-vinblastine are dissolved in 75 ml. of dimethyl formamide. Oxygen is bubbled through the solution slowly for 10 minutes, whereupon the reaction mixture is allowed to stand at room temperature for 16 to 20 hours. The pH is adjusted to 8.5 with a concentrated aqueous ammonium hydroxide solution. The alkaline mixture obtained is extracted with three 100-ml. portions of benzene. The combined extracts are dried with sodium sulphate, filtered and the filtrate is evaporated. The residue is dissolved in 3 ml. of ethanol and allowed to stand at 5° C. for 16 hours. The precipitated crystals are filtered off, washed with a small portion of cool methanol and dried. 0.366 mg. (61.0%) of the named compound is obtained.

EXAMPLE 20

Leurosine

Following the procedure described in the Example 19 but performing the oxidation in the presence of black platinum, the weight of which is equal to that of anhydrovinblastine, the reaction is completed within one hour.

Yield: 30.5% named compound.

EXAMPLE 21

Leurosine

Following the procedure described in the Example 19 but performing the oxidation in the presence of aluminium oxide used in a five-fold amount related to the anhydrovinblastine the title compound is prepared. The quality of the aluminium oxide employed corresponds to the activity grade I or II. The reaction is completed within two hours.

Yield: 30% named compound.

EXAMPLE 22

Leurosine

To a solution of 50 mg. of 3',4'-anhydro-vinblastine in 5 ml. of tetrahydrofuran 50 mg. of a 15% aqueous sodium hychlorite solution is added.

The epoxidation is completed at −10° C. (pH 8.5) within three to 10 minutes. The reaction mixture is extracted with three 10-ml. portions of benzene, The combined benzene extracts are dried with sodium sulphate, filtered and the filtrate is evaporated. The residue is crystallized from 1 ml. of ethanol.

Yield: 30% named compound.

EXAMPLE 23

N-desmethyl-N-formyl-leurosine

Leurosine prepared according to any of the Examples 12 to 15 or 18 to 21 is transformed to its sulphate salt in a conventional manner which is then further transformed following the reaction route outlined below:

To a solution of 12 g. (0.0132 moles) of leurosine sulphate in 2640 ml. of acetone glacial acetic acid distilled from 0.6 lit. of chromic acid is added. The solution is cooled to −55° C. and acetic anhydride containing 5.94 g. (0.135 moles) of chromic acid cooled to the same temperature are added within three minutes. The mixture is allowed to stand for an additional five minutes whereupon a sufficient amount (about 6 lit.) of deep-freezed concentrated ammonium hydroxide solution is carefully added to set the pH of the mixture to 6. During the neutralization care must be taken that the temperature of the mixture does not exceed +50° C. Thereafter 9 lit. of distilled water are added to the alkaline solution which is then further alkalized with an aqueous ammonium hydroxide solution till a pH of 8.5 is achieved.

The reaction mixture is extracted with four 1.5-lit. portions of methylene chloride, whereby the alkaloid base is transferred into the methylene chloride phase. The phases are allowed to separate and the combined organic phases are washed with three one-lit. portions of distilled water. The organic phase is then dried with sodium sulphate and evaporated to dryness under reduced pressure. 10 g. of a beige-white, dry residue are obtained identified as a mixture of crude N-desmethyl-N-formyl-leurosine and N-desmethylleurosine.

This residue is dissolved in a mixture of 60 ml. of concentrated formic acid and 10 ml. of acetic anhydride. The mixture is poured into 300 ml. of water cooled to 0° to +5° C. and the pH is subsequently adjusted to 9 by the addition of aqueous concentrated ammonium hydroxide solution having the same temperature, with stirring. The solution is then extracted with three 100-ml. portions of methylene chloride and the combined and dried methylene chloride extracts are evaporated to dryness under reduced pressure.

9.8 g. of amorphous, crude white N-desmethyl-N-formylleurosine are obtained.

The crude N-desmethyl-N-formyl-leurosine is purified by column chromatography in the following way. 9.8 g. of the crude N-desmethyl-N-formyl-leurosine are dissolved in 60 ml. of benzene and the solution is passed over a column of 45 mm. diameter filled with 500 g. aluminium oxide of III. activity grade. Elution is carried out subsequently with the solvent systems indicated in the following table.

| Composition of the eluting agent | Quantity (ml.) |
| --- | --- |
| Benzene | 1200 |
| 2:1 mixture of benzene:chloroform | 5000 |
| 1:1 mixture of benzene:chloroform | 3000 |
| chloroform | 800 |

400-ml. fractions of the eluate are pooled. N-desmethyl-N-formyl-leurosine is contained mainly in the fractions 15 to 20. The combined fractions containing N-desmethyl-N-formyl-leurosine are evaporated to dryness under reduced pressure. The obtained residue may optionally be transformed into a sulphuric acid addition salt in a manner described in the Example 8.

Yield: 7.10 g. (63.7%) of N-desmethyl-N-formyl-leurosinemonosulphate.

Melting point: 248° to 252° C.

What we claim is:

1. A process for preparing a compound of the formula Ia or an acid addition salt thereof

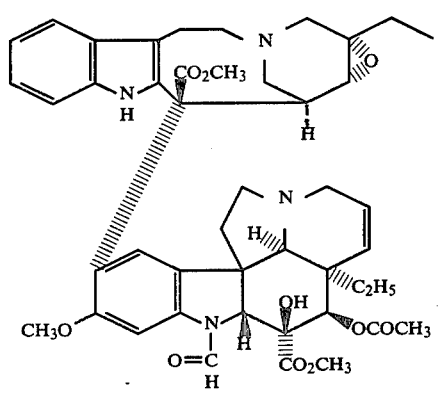
(Ia)

comprising the steps of
(a) dehydrating vincristine or vinblastine or an acid addition salt thereof with a sulfur or phosphorus halide or or oxyhalide in an organic solvent to produce a compound of formula II

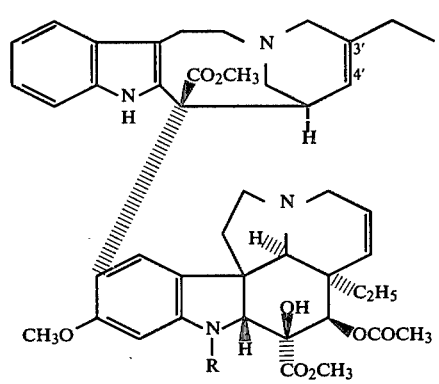
(II)

in which R is methyl when vinblastine is the starting material or is formyl when vincristine is the starting material;
(b) where R is methyl in formula II, oxidizing the compound of formula II with chromic acid to yield the compound of formula II where R is formyl; and
(c) selectively epoxidizing the double bond in the 3',4'-positions of the compound of formula II where R is formyl with an epoxidizing agent selected from the group consisting of oxygen, oxygen and an azo compound, cumyl hydroperoxide, and tert.-butyl hydroperoxide to yield the desired product.

2. The process defined in claim 1 wherein step (a) is carried out in dimethyl formamide.

3. The process defined in claim 1, step (c) where oxygen is used as the epoxidizing agent and dimethyl-formamide or a nitrile is employed as a solvent.

4. The process defined in claim 1, step (c), where oxygen and an azo compound are used as the epoxidizing agent and dimethyl formamide or a nitrile is employed as the solvent.

5. The process defined in claim 1, step (c), wherein cumyl hydroperoxide or tert.-butyl hydroperoxide is used as the epoxidizing agent and a nitrile or benzene or mixtures thereof are used as solvents.

6. A process for the preparation of a compound of formula Ia or an acid addition salt thereof;

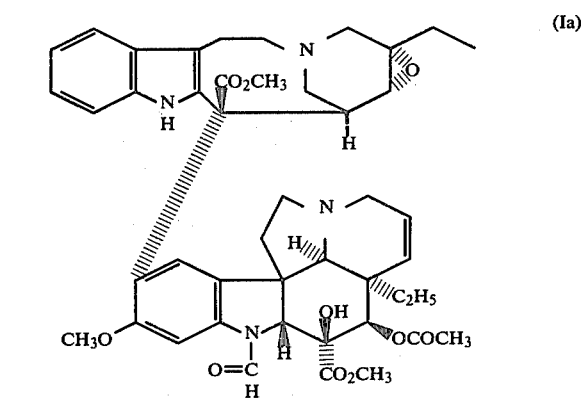
(Ia)

comprising the steps of
(a) coupling catharantine-N-oxide with N-desmethyl vindoline and subsequently adding an alkali metal borohydride to produce a compound of formula IIa

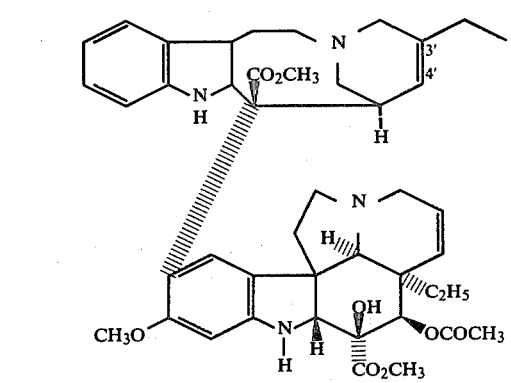

(b) selectively epoxidizing the compound formed during step (a) at the 3',4'-double bond in the presence of an acid with an epoxidizing agent selected from the group consisting of oxygen, oxygen and an azo compound, cumyl hydroperoxide and tert.-butyl hydroperoxide; and
(c) formylating the compound formed during step (b) with formic acid or with a mixture of formic acid and acetic anhydride to convert the NH group in the vindoline moiety to an N-CHO group thus yielding the desired product.

7. The process defined in claim 1, step (b) were oxygen is used as the epoxidizing agent and dimethyl formamide or a nitrile is used as a solvent.

8. The process defined in claim 1, step (b) where oxygen and an azo compound are used as the epoxidizing agent and dimethyl formamide or a nitrile is used as a solvent.

9. The process defined in claim 6, step (b), where cumyl hydroperoxide or tert.-butyl hydroperoxide is used as the epoxidizing agent and a nitrile compound, benzene or mixtures thereof are used as a solvent.

10. The process defined in claim 9 wherein the epoxidizing agent further comprises an azo compound.

11. A process for preparing a compound of formula Ia or an acid addition salt thereof

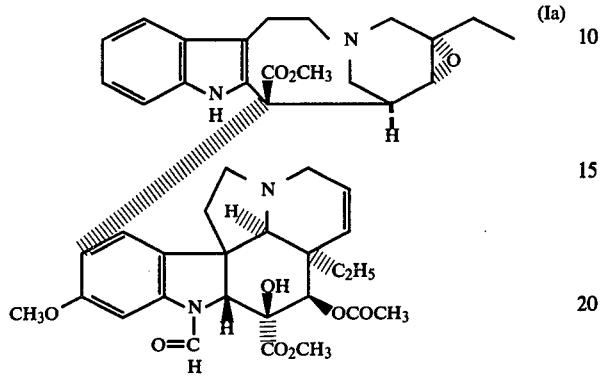

comprising the steps of:
(a) coupling catharantine-N-oxide with N-desmethyl vindoline, and subsequently adding an alkali metal borohydride to produce a compound of formula IIa

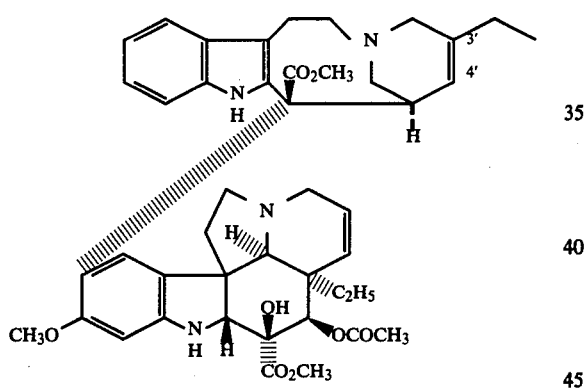

(b) formylating the compound formed during step (a) with formic acid or with a mixture of formic and acetic anhydride to convert the NH group of the vindoline moiety to an N-CHO group; and
(c) selectively epoxidizing the compound formed during step (b) at the 3',4'-double bond with an epoxidizing agent selected from the group consisting of oxygen, oxygen and an azo compound, cumyl hydroperoxide and tert.-butyl hydroperoxide to yield the desired product.

12. A process for preparing a compound of formula Ia or an acid addition salt thereof

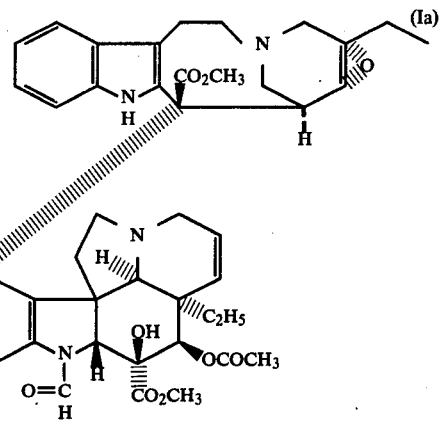

comprising the steps of:
(a) coupling catharantine-N-oxide with vindoline and subsequently adding an alkali metal borohydride to produce a compound of formula IIb

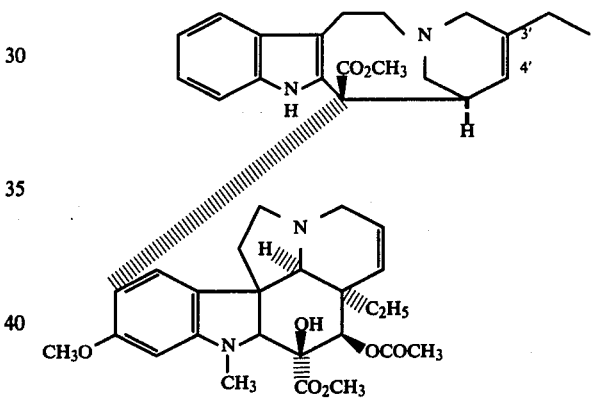

(b) selectively epoxidizing the compound of formula IIb in the 3',4'-double bond with an epoxidizing agent selected from the group consisting of oxygen, oxygen and an azo compound, cumyl hydroperoxide and tert.-butyl hydroperoxide wherein steps (a) and (b) are carried out in direct or reverse order; and
(c) oxidizing the N-CH3 moiety in the vindoline moiety to an N-CHO moiety with chromic aid to yield the desired compound.

* * * * *

UNITED STATES PATENT AND TRADEMARK OFFICE
CERTIFICATE OF CORRECTION

PATENT NO. : 4,199,505

DATED : 22 April 1980

INVENTOR(S) : Csaba Szántay et al

It is certified that error appears in the above-identified patent and that said Letters Patent are hereby corrected as shown below:

In the ABSTRACT, correct formula I to read:

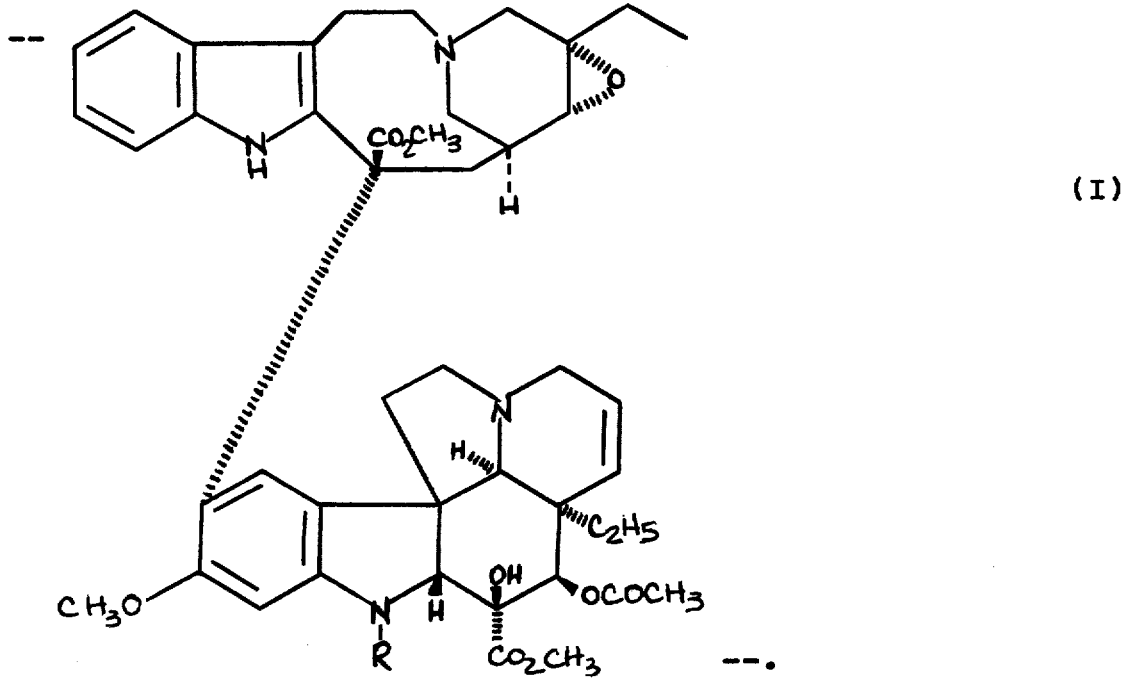

(I)

UNITED STATES PATENT AND TRADEMARK OFFICE
CERTIFICATE OF CORRECTION

PATENT NO. : 4,199,505
DATED : 22 April 1980
INVENTOR(S) : Csaba Szántay et al

It is certified that error appears in the above-identified patent and that said Letters Patent are hereby corrected as shown below:

Columns 4, 15, correct formula II to read:
--

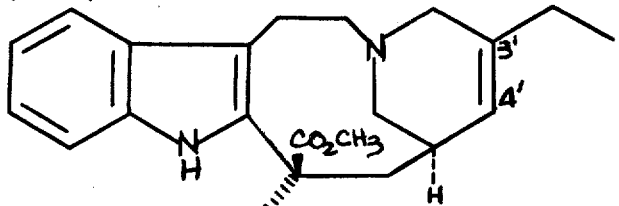

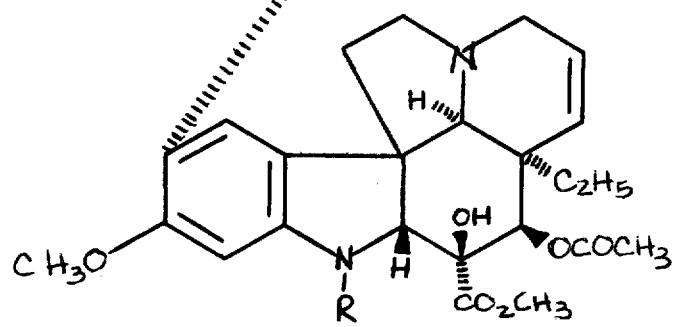

(II)

--.

UNITED STATES PATENT AND TRADEMARK OFFICE
CERTIFICATE OF CORRECTION

PATENT NO. : 4,199,505

DATED : 22 April 1980

INVENTOR(S) : Csaba Szántay et al

It is certified that error appears in the above-identified patent and that said Letters Patent are hereby corrected as shown below:

Columns 15, 16, 17, 18, correct formula Ia to read:

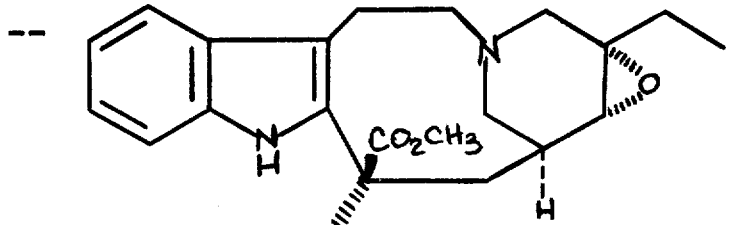

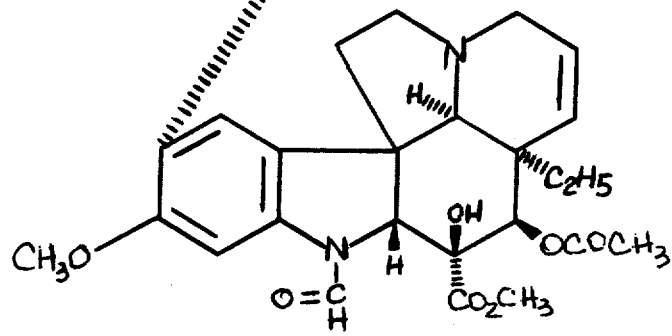

(Ia)

UNITED STATES PATENT AND TRADEMARK OFFICE
CERTIFICATE OF CORRECTION

PATENT NO. : 4,199,505
DATED : 22 April 1980
INVENTOR(S) : Csaba Szántay et al

It is certified that error appears in the above—identified patent and that said Letters Patent are hereby corrected as shown below:

Columns 16, 17, correct formula IIa to read:

--
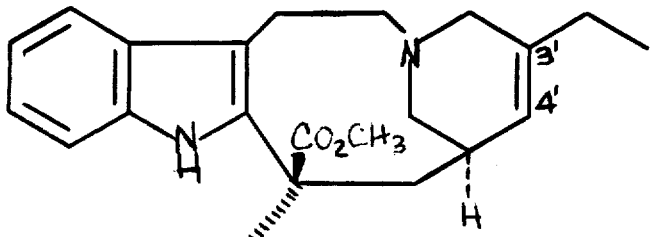
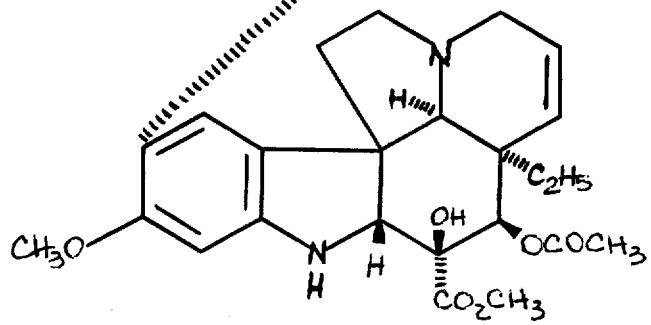

(IIa)

--.

UNITED STATES PATENT AND TRADEMARK OFFICE
CERTIFICATE OF CORRECTION

PATENT NO. : 4,199,505

DATED : 22 April 1980

INVENTOR(S) : Csaba Szántay et al

It is certified that error appears in the above-identified patent and that said Letters Patent are hereby corrected as shown below:

Column 18, correct formula IIb to read:

--

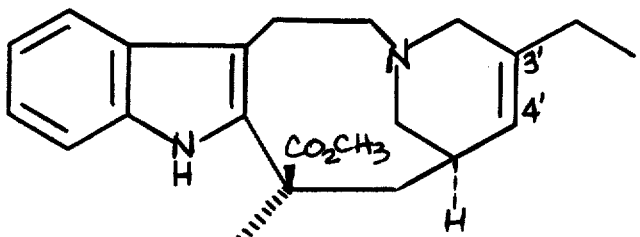

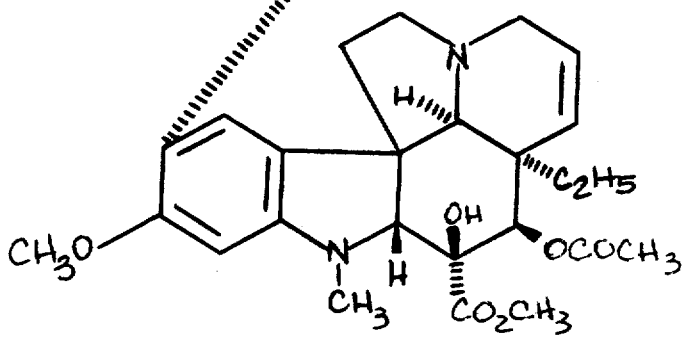

(IIb)

--.

Signed and Sealed this

Twelfth Day of August 1980

[SEAL]

Attest:

SIDNEY A. DIAMOND

Attesting Officer    Commissioner of Patents and Trademarks